United States Patent [19]

Knifton

[11] 4,265,828

[45] May 5, 1981

[54] MANUFACTURE OF ETHYLENE GLYCOL FROM SYNTHESIS GAS

[75] Inventor: John F. Knifton, Austin, Tex.

[73] Assignee: Texaco Development Corp., White Plains, N.Y.

[21] Appl. No.: 108,745

[22] Filed: Dec. 31, 1979

[51] Int. Cl.$^3$ ............................................. C07C 27/06
[52] U.S. Cl. ............................ 260/449 L; 260/449 R; 260/449.5; 252/431 C; 252/441; 252/443; 252/472
[58] Field of Search ............. 260/449 L, 449 R, 449.5

[56] References Cited

U.S. PATENT DOCUMENTS 2,636,046   4/1953   Gresham ....................... 260/449.6 R
4,170,605  10/1979   Williamson et al. ............. 260/449 L

*Primary Examiner*—Howard T. Mars
*Attorney, Agent, or Firm*—Carl G. Ries; Robert A. Kulason; James L. Bailey

[57] ABSTRACT

This invention concerns a process of making ethylene glycol which comprises the steps of contacting a mixture of CO and $H_2$ with a catalyst system comprising a ruthenium-containing compound dispersed in a low melting quaternary phosphonium or ammonium base or salt, and heating said resultant reaction mixture under a pressure of 500 psi or greater at a temperature of at least 150° C. for a sufficient time to provide said ethylene glycol.

12 Claims, No Drawings

4,265,828

MANUFACTURE OF ETHYLENE GLYCOL FROM SYNTHESIS GAS

SUMMARY AND BACKGROUND OF THE INVENTION

This invention concerns an improved process for preparing ethylene glycol by reaction of oxides of carbon with hydrogen in presence of a catalyst system.

There are ever-increasing efforts to provide new methods of making ethylene glycol particularly useful as a component in polyester fiber and antifreeze formulations. An ever present aim is to prepare said glycol in relatively high yields involving a catalyst system providing good selectivity.

One proposed mode of making ethylene glycol is the reaction of carbon monoxide and hydrogen in presence of variously proposed catalyst systems. The mixture of carbon monoxide and hydrogen, commonly known as synthesis gas, is reacted at elevated pressures and temperatures. For example, in Belgium Pat. No. 793,086 and U.S. Pat. No. 3,940,432 there is described the cosynthesis of methanol and ethylene glycol from mixtures of carbon monoxide and hydrogen using a complex rhodium catalyst. While other metals of group VIII of the Periodic Table have been tested for activity under similar conditions, including cobalt, ruthenium, copper, manganese, iridium and platinum, only cobalt was found to have slight activity. The use of ruthenium compounds in particular failed to produce polyfunctional products such as ethylene glycol. This is illustrated in U.S. Pat. No. 3,833,634 for solutions of triruthenium dodecarbonyl.

This invention therefore is to provide a process of making ethylene glycol by resort to a unique catalyst system which produces said glycol in good yields and selectivity. Other objects will appear hereinafter.

SUMMARY OF THE INVENTION

This invention concerns a method for making ethylene glycol which comprises the steps of contacting a mixture of CO and $H_2$ with a catalyst system composed of a ruthenium-containing compound dispersed in a low melting quaternary phosphonium or ammonium base or salt and heating said resultant reaction mixture under a pressure of 500 psi or greater at a temperature of at least 150° C. for a sufficient time to provide said ethylene glycol.

DETAILED DESCRIPTION OF THE INVENTION

In the narrower and more preferred practice of this invention, ethylene glycol and ethylene glycol monoalkylethers are prepared concurrently from a synthesis gas mixture of carbon monoxide and hydrogen by a process comprising the following steps:

(a) Contacting said mixture of carbon monoxide and hydrogen with a catalyst system composed of a ruthenium-containing compound dispersed in a low melting quaternary phosphonium base or salt of an organic or mineral acid.

(b) Heating said reaction mixture to a temperature of between 180° and 250° C., at superatmospheric pressures of 2000 psi or greater with sufficient carbon monoxide and hydrogen to satisfy the stoichiometry of the desired glycol syntheses, until substantial formation of the desired ethylene glycol and ethylene glycol monoalkylethers has been achieved, and (c) Preferably isolating said ethylene glycol and ethylene glycol monoalkylethers contained therein.

In order to present the inventive concept in the greatest possible detail as to promote its understanding, the following supplementary disclosure is submitted. The basic invention, improved upon here is practiced as follows:

Catalysts that are suitable in the practice of this invention contain ruthenium. The ruthenium-containing catalyst may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise ruthenium in complex combination with carbon monoxide and hydrogen. The most effective catalysis is believed to be achieved where ruthenium hydrocarbonyl species are solubilized in a quaternary salt under reaction conditions.

The ruthenium catalyst precursors may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium(II)iodide, anhydrous ruthenium(III) chloride and ruthenium nitrate, or as the salt of a suitable organic carboxylic acid, for example, ruthenium(III) acetate napththenate, ruthenium valerate and ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Ruthenium complexes containing Group VB Donor ligands such as triphenylphosphine may be effective catalyst precursors under certain conditions.

Preferred ruthenium-containing compounds include oxides of ruthenium, ruthenium salts of a mineral acid, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl. The usefulness of these ruthenium precursors for ethylene glycol synthesis is illustrated by the accompanying Examples 1-8.

The ruthenium-containing compound is, prior to its catalytic use in making ethylene glycol, first dispersed in a low melting quaternary phosphonium or ammonium base or salt. It is interesting to note that the ruthenium-containing compound alone, without being dispersed in said salt or base, has little, if any activity in promoting the manufacture of ethylene glycol from synthesis gas.

The quaternary phosphonium or ammonium base or salt must be relatively low melting, that is, melt at a temperature less than about the temperature of reaction of making ethylene glycol. Usually the quaternary compound has a melting point less than about 180° C., and most often has a melting point less than 150° C.

Suitable quaternary phosphonium salts have the formula:

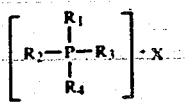

where $R_1$, $R_2$, $R_3$ and $R_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance. Also useful are the corresponding quaternary ammonium bases and salts in the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus or nitrogen atom through the aryl function.

Illustrative examples of suitable quaternary phosphonium and ammonium bases and salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutylammonium bromide and tetramethylammonium hydroxide, pentahydrate and trimethyldodecylammonium bromide. Tables II and III provide evidence of the effectiveness of these quaternary ammonium and phosphonium salts and bases when in combination with ruthenium(IV) oxide and ruthenium(III) chloride.

The preferred quaternary salts are generally the tetralkylphosphonium salts containing alkyl groups having 1-6 carbon atoms, such as methyl, ethyl, and butyl. Tetrabutylphosphonium salts, such as tetrabutylphosphonium bromide, are most preferred for the practice of this invention.

Preferred tetrabutylphosphonium salts or bases include the bromide, chloride, iodide, acetate and chromate salts and hydroxide base.

The quantity of ruthenium catalyst (exclusive of quaternary salt) employed in the instant invention is not critical and may vary over a wide range. In general, the novel process is desirably conducted in the presence of a catalytically effective quantity of the active ruthenium species which gives the desired products in reasonable yields. The reaction proceeds when employing as little as about $1 \times 10^{-6}$ weight percent, and even lesser amounts, of ruthenium, basis the total weight of the reaction mixture. The upper concentration is dictated by a variety of factors including catalyst cost, partial pressures of carbon monoxide and hydrogen, operating temperature etc. A ruthenium catalyst concentration of from about $1 \times 10^{-5}$ to about 30 weight percent ruthenium, based on the total weight of reaction mixture is generally desirable in the practice of this invention.

The temperature range which can usefully be employed in these syntheses is a variable dependent upon other experimental factors, including the pressure, and the concentration and choice of the particular species of ruthenium catalyst among other things. The range of operability is from about 150° to 350° C. when superatmospheric pressure of syngas are employed. A narrow range of 180°-250° C. represents the preferred temperature range. This narrower range is illustrated by the data in the accompanying Table IV.

Superatmospheric pressures of 500 psi or greater lead to substantial yields of ethylene glycol by the process of this invention. A preferred operating range is from 2000 psi to 9000 psi, although pressures above 9000 psi also provide useful yields of desired glycol.

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of the desired ethylene glycol reaction (eq. 1).

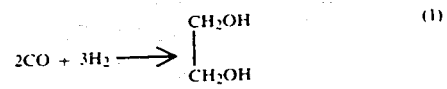

Ethylene glycol derivatives may also be formed during the course of this desired ethylene glycol syntheses. Most often these derivatives are ethylene glycol monoalkylethers, they typically include ethylene glycol monoethyl ether, ethylene glycol monoethyl ether and ethylene glycol monopropyl ether. The relative concentrations of ethylene glycol and its monoalkyl ether derivatives is the crude liquid product which are illustrated in the accompanying Tables I and II for a variety of catalyst systems comprising various ruthenium compounds dispersed in low melting quaternary phosphonium or ammonium bases and salts. Where the low melting quaternary ammonium or phosphonium salt is a carboxylic acid salt, the crude liquid product mixture may also contain significant quantities of ethylene glycol acid esters, particularly ethylene glycol mono and diesters. Table III illustrates the cosyntheses of ethylene glycol, ethylene glycol monoacetate and diacetate esters; here the ruthenium catalyst precursors are dispersed in a low melting quaternary phosphonium acetate, tetrabutylphosphonium acetate.

The major by-products of these glycol syntheses are most commonly methanol, ethanol and n-propanol, which are, of course, also useful compounds and major articles of commerce. The alkanols, ethylene glycol and ethylene glycol monoalkyl ethers can easily be separated from one another by conventional means, eg. fractional distillation in vacuo.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired glycol product, and said material may be recovered by methods well known in the art, such as distillation, fractionation, extraction and the like. A fraction rich in ruthenium catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psi).

Having described the inventive process in general terms, the following examples are submitted to supply specific and illustrative embodiments.

EXAMPLE 1

Anhydrous ruthenium(IV) dioxide (75% Ru, 4 mmole) dispersed in solid tetrabutylphosphonium bromide (15 g, 44.2 mmole, m.p.=100° C.) was transferred in a glass liner to an 850 ml pressure reactor equipped with heating and means of agitation. The reactor was sealed, flushed with $CO/H_2$ (1:1). The mixture was heated to 220° C. with rocking, the pressure raised to 430 atm by $CO/H_2$ addition from a large surge tank, and the reactor held at room temperature for 18 hr. Pressure in the reactor was maintained at ca. 430 atm by incremental additions of $CO/H_2$ from the surge tank.

On cooling, the reactor pressure (185 atm) was noted, a typical gas sample taken and the excess gas removed. The reddish-brown liquid product (41.3 g) showed only a trace of a black solid phase. The liquid yield increase is 166%.

Analysis of the liquid product by GLC shows the presence of:
- 13.4 wt% ethylene glycol
- 20.2 wt% glycol ethers
- 21.4 wt% ethanol
- 30.1 wt% methanol The ethylene glycol and glycol ether fractions were recovered from the crude liquid product by fractional distillation in vacuo. Distillate fractions typically show an ethylene glycol content of >80%.

EXAMPLE 2

Ruthenium(IV) dioxide hydrate (53% Ru, 8 mmole) dispersed in tetrabutylphosphonium bromide (30 g) was transferred in a glass liner to the 850 ml pressure reactor. Said reactor was sealed, flushed with $CO/H_2$ and pressured to 136 atm with 1:1 $CO/H_2$. The mixture was heated to 220° C. with rocking, the pressure raised to 430 atm by $CO/H_2$ addition from the surge tank, and the reactor held at temperature for 6 hr. Pressure within the reactor was maintained at ca 430 atm by incremental additions of $CO/H_2$ from the surge tank.

On cooling, the reactor pressure (215 atm) was noted, a typical gas sample taken, and the excess gas removed. The deep-red liquid product (62.1 g) showed no evidence of a solid phase. The liquid yield increase was 97%.

Analysis of the liquid product by GLC shows the presence of:
- 17.1 wt% ethylene glycol
- 10.0 wt% glycol ethers
- 28.7 wt% ethanol
- 27.8 wt% methanol The ethylene glycol and glycol ethers were recovered from the crude liquid product together with the ethanol and methanol by fractional distillation in vacuo. Upon cooling, the residual ruthenium catalyst dispersed in tetrabutyl phosphonium bromide was recovered as a dark-red crystalline solid (32 g) having a m.p. of ca. 80° C.

EXAMPLE 3

Ruthenium(IV) dioxide, hydrate (53% Ru, 5 mmole) dispersed in tetrabutylphosphonium acetate (20 g, freshly recrystallized from butyl acetate) was transferred in a glass liner to an 850 ml pressure reactor equipped with heating and means of agitation. The reactor was sealed, flushed with $CO/H_2$ and pressured to 136 atm with $CO/H_2$ (1:1). The mixture was heated to 220° C. with rocking, the pressure raised to 430 atm by $CO/H_2$ addition from a large surge tank, and the reactor held at temperature for 18 hr. Pressure was maintained at about 425 atm by incremental additions of $CO/H_2$ from the surge tank.

On cooling, the reactor pressure (225 atm) was noted, a typical gas sample taken and the excess gas vented. The dark-brown liquid product (33.3 gm) showed no evidence of a solid phase.

Analysis of the liquid product by GLC shows the presence of:
- 17.0 wt% ethylene glycol plus glycol acetates
- 30.7 wt% methanol
- 11.7 wt% methyl acetate As can be seen from Examples 1 and 2 ethylene glycol and ethylene glycol monoalkyl ethers are consistently major products of the syntheses of the invention. Both products may be isolated by vacuum distillation. The residual ruthenium melt catalyst or ruthenium-containing compound dispersed in the low melting quaternary phosphonium salt then resolidifies upon cooling.

Example 3 demonstrates that substantial amounts of ethylene glycol and its acetate esters are formed using a 1:1 syngas mixture and a phosphonium acetate quaternary.

EXAMPLES 4–9

Table I below further illustrates the invention in setting forth still further process variations for a variety of ruthenium catalyst precursors. Of particular note, in Example 5, using a dispersion of ruthenium(III) acetylacetonate in tetrabutylphosphonium bromide, the quantity of liquid product (95.2 g) corresponds to a 186% weight increase over the catalyst charged at the beginning of the run. The calculated total ethylene glycol yield (glycol plus glycol compound composed of the monoalkyl ether fractions) is 0.15 mole. A 6 hr. run using a similar catalyst combination (Example 7) produces a 116% weight gain.

Recycle of a ruthenium(IV) oxide, tetrabutylphosphonium bromide dispersion is illustrated in Examples 4 and 9. Here the charge in Example 9 is the crystalline red solid residue (31.9 g) from Example 4, after fractional distillation of the crude liquid product (71.9 g) to remove the volatile organic fractions (alkanols, ethylene glycol etc.).

ethylene glycol synthesis. The nitrogen or phosphorus may be bonded to alkyl and aryl radicals and a variety of counterions may be employed including halide, nitrate, chromate and perfluoroborate. Of particular note, the ruthenium(IV) dioxide in combination with tetrabutylphosphonium iodide (Example 12) generates a 312% liquid yield gain.

TABLE II[a]

| Example | Ruthenium Source | Quaternary Salt | mp. | CO/$H_2$ | Max. Pres. (psi) | Temp °C. | Time hr. | Procedure | Liquid Yield Increase(%) |
|---|---|---|---|---|---|---|---|---|---|
| 10 | $RuO_2$ | $HpPh_3PBr$[c] | 179 | 1/1 | 6350 | 220 | 18 | C.P. | 41 |
| 11 | $RuO_2$ | $Bu_4PCl$ | | 1/1 | 6350 | 220 | 18 | C.P. | 82 |
| 12 | $RuO_2$ | $Bu_4PI$ | 96 | 1/1 | 6375 | 220 | 18 | C.P. | 312 |
| 13 | $RuO_2$ | $Bu_4PNO_3$ | | 1/1 | 6375 | 220 | 18 | C.P. | 59 |
| 14 | $RuO_2$ | $Bu_4POH$ | | 1/1 | 6320 | 220 | 18 | C.P. | 83 |
| 15 | $RuO_2$ | $Bu_4PF$ | | 1/1 | 6325 | 220 | 18 | C.P. | 62 |
| 16 | $RuO_2$ | $Bu_4PCrO_4$ | 140 | 1/1 | 6385 | 220 | 18 | C.P. | 54 |
| 17 | $RuO_2$ | $Bu_4PBF_4$ | 95 | 1/1 | 6370 | 220 | 18 | C.P. | 11 |
| 18 | $RuO_2$ | $Bu_4NBr$ | 103 | 1/1 | 6350 | 220 | 18 | C.P. | 29 |
| 19 | $RuO_2$ | $Me_3RNBr$[d] | 61 | 1/1 | 6325 | 220 | 18 | C.P. | 76 |
| 20 | $RuO_2$ | $Me_4NOH$ | 62 | 1/1 | 6475 | 220 | 18 | C.P. | <5 |

| Example | $H_2O$ | MeOH | EtOH | PrOH | EGMME | EG | EGMEt | EGMPr |
|---|---|---|---|---|---|---|---|---|
| 10 | (0.8) | | 1.4 | 1.2 | 5.6 | 1.4 | 8.7 | 3.2 |
|    | (10.1) | 1.8 | 12.1 | 9.1 | 3.1 | | 4.5 | 1.0 |
| 11 | 4.8 | 5.5 | 20.4 | 4.0 | 6.3 | 6.4 | 2.2 | 1.2 |
| 12 | 1.3 | 40.6 | 38.1 | 3.3 | 2.8 | 1.7 | 3.8 | 0.2 |
| 13 | 1.1 | 50.5 | 13.7 | 0.6 | | 0.1 | | |
| 14 | 3.2 | 52.9 | 13.3 | 0.7 | 2.8 | 3.7 | 2.5 | 0.5 |
| 15 | 20.4 | 59.9 | 4.3 | 0.7 | | 0.1 | 0.1 | |
| 16 | 26.7 | 8.2 | 16.5 | 1.9 | 5.8 | 7.4 | 2.1 | 0.7 |
| 17 | 28.1 | 44.9 | 3.0 | 1.0 | 1.5 | 0.4 | 0.4 | |
| 18 | 12.2 | 0.5 | | | 0.9 | 1.2 | | |
| 19 | 1.2 | 57.8 | 11.6 | 4.1 | 1.3 | 1.9 | 1.4 | 0.6 |
| 20 | 13.9 | 36.3 | | | 0.1 | 1.9 | 0.1 | |

[a]Typical operating conditions: 2-8 mmole $RuO_2$ . $XH_2O$, 10-30g quaternary salt, C.P. = Constant Pressure.
[b]EG, Ethylene Glycol; EGMME, Ethylene Glycol Monomethyl Ether; EGMEE, Ethylene Glycol Monoethyl Ethyl; EGMPr, Ethylene Glycol Monopropyl Ether.
[c]Heptyltriphenylphosphonium bromide.
[d]Trimethyldodecylammonium bromide.

TABLE I

| | CATALYST COMPOSITION | | | | LIQUID PRODUCT COMPOSITION (WT%) | | | | | | | |
|---|---|---|---|---|---|---|---|---|---|---|---|---|
| Example[a] | Ruthenium Source | Quaternary Salt | mp. | Liquid Yield Increase (%) | $H_2O$ | MeOH | EtOH | PrOH | EGMME[c] | EG[d] | EGMEt[e] | EGMPr[f] |
| 4[b] | $RuO_2$ . $XH_2O$ | $Bu_4PBr$ | 100° | 127 | 6.0 | 31.4 | 30.6 | 3.2 | 8.1 | 9.4 | 3.8 | |
| 5 | $Ru(Acac)_3$ | $Bu_4PBr$ | 100° | 186 | 1.5 | 26.1 | 33.4 | 5.0 | 9.7 | 5.6 | 6.5 | 1.4 |
| 6 | $RuCl_3$ . $XH_2O$ | $Bu_4PBr$ | 100° | 24 | 58.5 | | 0.4 | 0.5 | 0.9 | 1.1 | | |
| 7[g] | $Ru(Acac)_3$ | $Bu_4PBr$ | 100° | 116 | 1.8 | 35.3 | 22.8 | 2.7 | 7.4 | 9.5 | 4.1 | 1.1 |
| 8 | $Ru_3(CO)_{12}$ | $Bu_4PBr$ | 100° | 160 | 2.2 | 31.5 | 32.7 | 3.3 | 8.7 | 6.0 | 4.7 | 0.8 |
| 9[b] | 4, Recycle[h] | | ≈80° | 102 | 4.7 | 31.5 | 29.5 | 2.7 | 8.7 | 9.6 | 3.9 | 0.5 |

[a]Operating conditions: 8 mmole Ru; 30g $Bu_4PBr$; 1:1 CO/$H_2$ syngas; Ca 430 atm constant pressure, 220° C., 18 hr.
[b]Ca 475 atm constant pressure, 12 hr.
[c]EGMME = Ethylene glycol monomethyl ether.
[d]EG = Ethylene glycol
[e]EGMMEt = Ethylene glycol monoethyl ether.
[f]EGMPr = Ethylene glycol monopropyl ether.
[g]4 mmole Ru; 15g $Bu_4PBr$; 6 hr.
[h]Residual ruthenium catalyst after recovery of organic products of fractional distillation in vacuo.

EXAMPLES 10-20

Table II below illustrates still further variations of the invention in terms of types of quaternary salts and bases that may be employed, and process variables of time, temperature and pressure. Both quaternary ammonium and phosphonium salts have been found effective for

EXAMPLES 21-24

The versatility of the invention is further illustrated by the runs summarized below in Table III. There the ruthenium is dispersed in tetrabutylphosphonium acetate, and the liquid organic product fraction contains ethylene glycol, its monoalkylether derivatives, as well as the ethylene glycol monoacetate and diacetate esters.

TABLE III[a]

TABLE III[a]-continued

| Example | Ruthenium Source | Quaternary Salt | m.p. | CO/H$_2$ | Pres. (psi) | Temp °C. | hr. | Procedure[c] | Yield Increase(%) |
|---|---|---|---|---|---|---|---|---|---|
| 21 | RuCl$_3$ . XH$_2$O | Bu$_4$POAc | 73 | 1:1 | 6525 | 220 | 18 | V.P. | 42 |
| 22 | RuCl$_3$ . XH$_2$O | Bu$_4$POAc | 73 | 1:1 | 6325 | 220 | 18 | C.P. | 93 |
| 23 | RuCl$_3$ . XH$_2$O | Bu$_4$POAc | [d] | 1:1 | 6370 | 220 | 18 | C.P. | 34 |
| 24 | RuO$_2$ . XH$_2$O | Bu$_4$POAc | 73 | 1:1 | 6450 | 220 | 18 | C.P. | 59 |

| | ←LIQUID PRODUCT COMPOSITION (WT%) → | | | | | | | | |
|---|---|---|---|---|---|---|---|---|---|
| Example | H$_2$O | MeOH | EtOH | MeOAc | EtOAc | E.G. | EGOAc[b] | EGOAc$_2$[b] | EGMME |
| 21 | 1.3 | 31.3 | 9.2 | 33.1 | 2.1 | 2.6 | 2.9 | | |
| 22 | 2.0 | 34.9 | 6.7 | 17.3 | 1.0 | 4.4 | 3.9 | | 2.2 |
| 23 | 0.5 | 42.2 | 8.5 | 22.0 | 1.1 | 2.1 | 2.4 | | 2.1 |
| 24 | 1.8 | 30.7 | 3.3 | 11.7 | | 5.0 | 10.1 | 1.9 | 0.4 |

[a]Run Conditions: 5.0 mmole Ru, 20g Bu$_4$POAc; Designations as per Table I.
[b]EGOAc, Ethylene glycol monoacetate; EGOAc$_2$, ethylene glycol diacetate.
[c]Procedure - V.P. = Variable Pressure; CP = Constant Pressure.
[d]Crude commercial sample of tetrabutylphosphonium acetate (95% purity), liquid at room temp.

EXAMPLES 25-39

Table IV below summarizes still further runs using the ruthenium(IV) oxide tetrabutylphosphonium bromide dispersion. Runs 25-29 show the effect of changing the CO/H$_2$ gas composition upon product distribution. Runs 30 and 31 illustrate that the ruthenium to phosphonium quaternary ratio may be varied without departing from the scope of the invention. Runs 32-39 show that the operating pressure, temperature as well as reaction times may again be widely varied without departing from the scope of the invention.

It may be noted that in experiment 30 the concentrations of ethylene glycol and ethylene glycol monoalkylethers in the liquid product are 17.6 and 11.5 wt% respectively. The estimated total weight rates of ethylene glycol-to-alkanol is 1:1.9.

Finally the invention is advantageous in that numerous substitutions, modifications and changes can be made without departing from the inventive concept. However, the scope of the subject invention may best be understood by examining the claims which follow read in conjunction with the preceding specification.

It is claimed:

1. A process of making ethylene glycol which comprises the steps of contacting a mixture of CO and H$_2$ with a catalyst system comprising a ruthenium-containing compound dispersed in a low melting quaternary phosphonium or ammonium base or salt and heating said resultant reaction mixture under a pressure of 500 psi or greater at a temperature of at least 180° C. for a sufficient time to provide said ethylene glycol.

2. The process of claim 1 wherein said quaternary salt or base has a melting point less than about 180° C.

TABLE IV[a]

| Example | Ruthenium Source | Quaternary Salt | mp. | CO/H$_2$ | Max. Pres. (psi) | Temp °C. | Time hr. | Procedure | Liquid Yield Increase(%) |
|---|---|---|---|---|---|---|---|---|---|
| 25 | RuO$_2$ | Bu$_4$PBr | 100 | 2:3 | 7325 | 220 | 6 | V.P. | 50 |
| 26 | RuO$_2$ | Bu$_4$PBr | 100 | 1:1 | 6300[b] | 220 | 6 | C.P. | 90 |
| 27 | RuO$_2$ | Bu$_4$PBr | 100 | 1:1 | 7525 | 220 | 6 | V.P. | 54 |
| 28 | RuO$_2$ | Bu$_4$PBr | 100 | 3:2 | 7910 | 220 | 6 | V.P. | 45 |
| 29 | RuO$_2$ | Bu$_4$PBr | 100 | 7:3 | 7920 | 220 | 6 | V.P. | 30 |
| 30 | RuO$_2$ | ½ Bu$_4$PBr | 100 | 3:2 | 8060 | 220 | 6 | V.P. | 65 |
| 31 | RuO$_2$ | 2 Bu$_4$PBr | 100 | 3:2 | 7475 | 220 | 6 | V.P. | 18 |
| 32 | RuO$_2$ | Bu$_4$PBr | 100 | 3:2 | 7500 | 180 | 6 | V.P. | 22 |
| 33 | RuO$_2$ | Bu$_4$PBr | 100 | 3:2 | 7500 | 200 | 6 | V.P. | 35 |
| 34 | RuO$_2$ | Bu$_4$PBr | 100 | 3:2 | 7750 | 250 | 6 | V.P. | 49 |
| 35 | RuO$_2$ | Bu$_4$PBr | 100 | 3:2 | 8825 | 220 | 6 | V.P. | 63 |
| 36 | RuO$_2$ | Bu$_4$PBr | 100 | 3:2 | 6750 | 220 | 6 | V.P. | 38 |
| 37 | RuO$_2$ | Bu$_4$PBr | 100 | 3:2 | 3200 | 220 | 6 | V.P. | 16 |
| 38 | RuO$_2$ | Bu$_4$PBr | 100 | 3:2 | 7730 | 220 | 4 | V.P. | 37 |
| 39 | RuO$_2$ | Bu$_4$PBr | 100 | 3:2 | 7675 | 220 | 2 | V.P. | 27 |

| | ←COMPOSITION-LIQUID PRODUCT (WT%) → | | | | | | | |
|---|---|---|---|---|---|---|---|---|
| Example | H$_2$O | MeOH | EtOH | PrOH | EGMME | EG | EGMEt | EGMPr |
| 25 | 3.9 | 33.6 | 29.6 | 2.1 | 6.2 | 5.6 | 3.7 | 0.6 |
| 26 | 4.4 | 35.4 | 33.2 | 4.2 | 2.0 | 5.5 | 4.3 | 0.8 |
| 27 | 1.5 | 30.3 | 21.5 | 2.7 | 2.5 | 6.9 | 11.5 | 3.2 |
| 28 | 0.6 | 25.0 | 24.3 | 5.5 | 12.0 | 4.5 | 6.9 | 1.3 |
| 29 | 0.6 | 18.0 | 16.1 | 2.4 | 12.6 | 1.9 | 6.3 | 2.9 |
| 30 | 1.9 | 20.0 | 20.1 | 4.8 | 8.9 | 17.6 | 2.4 | 0.2 |
| 31 | 1.3 | 14.9 | 26.2 | 4.0 | 6.6 | 2.7 | 6.9 | 1.4 |
| 32 | 0.8 | 19.3 | 17.1 | 2.0 | 19.0 | 0.8 | 2.2 | 1.4 |
| 33 | 0.7 | 21.7 | 18.3 | 2.2 | 14.9 | 14.0 | 2.8 | 0.9 |
| 34 | 0.4 | 14.9 | 27.3 | 8.5 | 16.4 | 0.4 | 8.9 | 0.1 |
| 35 | 0.8 | 23.8 | 28.6 | 4.1 | 17.5 | 1.5 | 3.6 | 0.2 |
| 36 | 3.3 | 27.6 | 25.1 | 3.3 | 11.3 | 2.6 | 4.1 | 1.2 |
| 37 | 0.4 | 25.3 | 28.2 | 4.8 | 8.5 | 0.4 | 5.3 | 0.5 |
| 38 | 1.1 | 32.0 | 23.2 | 2.1 | 15.9 | 8.1 | 7.2 | 0.7 |
| 39 | 0.9 | 21.3 | 21.4 | 4.1 | 12.9 | 13.4 | 6.3 | 1.0 |

[a]Run Conditions: 2.7 mmole RuO$_2$ . XH$_2$O; 10g Bu$_4$PBr, Designations as per Table I.
[b]Typical Off-gas Composition: 42.4% H$_2$, 51.5% CO, 4.1% CO$_2$, 0.2% CH$_4$ 3. The process of claim 2 wherein said quaternary salt is a tetraalkylphosphonium salt.

4. The process of claim 3 wherein said alkyl groups contain 1-6 carbon atoms.

5. The process of claim 2 wherein said quaternary is a mixed alkylaryl phosphonium quaternary.

6. The process of claim 4 wherein said quaternary salt is tetrabutylphosphonium salt.

7. The process of claim 1 wherein the ruthenium-containing compound is selected from the group consisting of one or more oxides of ruthenium, ruthenium salts of a mineral acid, ruthenium salts of an organic carboxylic acid and ruthenium carbonyl or hydrocarbonyl derivatives.

8. The process of claim 7 wherein the ruthenium-containing compound is selected from the group consisting of anhydrous ruthenium(IV) dioxide, ruthenium(IV) dioxide hydrate, ruthenium(VIII) tetraoxide, ruthenium(III) trichloride hydrate, ruthenium acetate, ruthenium propionate, ruthenium(III) acetylacetonate and triruthenium dodecarbonyl.

9. The process of claim 8 wherein said ruthenium-containing compound is ruthenium(IV) dioxide.

10. The process of claim 8 wherein said ruthenium-containing compound is ruthenium(III) trichloride.

11. The process of claim 6 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

12. The process of claim 1 wherein said quaternary phosphonium base is tetrabutylphosphonium hydroxide.

* * * * *